United States Patent [19]

Cossaboon

[11] 4,185,036

[45] Jan. 22, 1980

[54] HYDROGENATION OF MIXED AROMATIC NITROBODIES

[75] Inventor: Karl F. Cossaboon, Fairville, Pa.

[73] Assignee: E. I. Du Pont de Nemours and Company, Wilmington, Del.

[21] Appl. No.: 837,633

[22] Filed: Sep. 28, 1977

Related U.S. Application Data

[63] Continuation-in-part of Ser. No. 429,196, Dec. 28, 1973, abandoned.

[51] Int. Cl.$^2$ ............................................. C07C 85/11
[52] U.S. Cl. ..................................... 260/580; 562/458
[58] Field of Search ......................................... 260/580

[56] References Cited

U.S. PATENT DOCUMENTS

| | | | |
|---|---|---|---|
| 2,252,099 | 8/1941 | Rosen | 260/580 |
| 2,402,423 | 6/1946 | Mason | 260/580 |
| 2,894,036 | 7/1959 | Graham | 260/580 |
| 3,230,259 | 1/1966 | Levy | 260/580 |
| 3,499,034 | 3/1970 | Gonzalez | 260/580 |

Primary Examiner—Winston A. Douglas
Assistant Examiner—John Doll

[57] ABSTRACT

Process, batch or continuous, for hydrogenating a mixture of an aromatic mononitro-non-amino compound and an aromatic dinitro and/or an aromatic mononitromonoamino compound, which process comprises reacting hydrogen and a homogeneous or heterogeneous liquid mixture of at least 25 weight % of an aromatic mononitro-non-amino compound and at least 25 weight % of at least one compound selected from aromatic dinitro compounds and aromatic mononitromonoamino compounds, for example, a 25:75 weight % mixture of p-nitroaniline and o-nitrotoluene, with vigorous mixing, in the presence of 0.05–1.0 weight % of an hydrogenation catalyst derived from a metal of Group VIII of the Periodic Chart of the Elements, at a temperature of 75°–225° C. and a pressure of 50–800 p.s.i.g.

14 Claims, 1 Drawing Figure

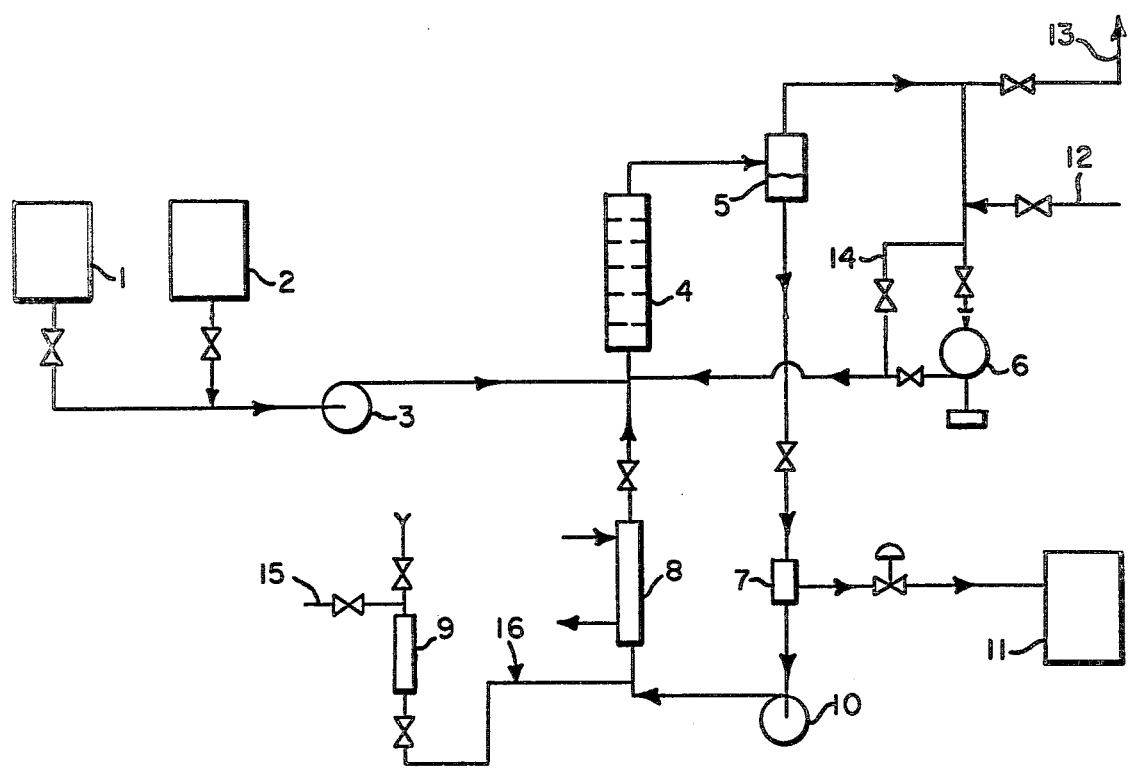

HYDROGENATION OF MIXED AROMATIC NITROBODIES

CROSS-REFERENCE TO RELATED APPLICATION

This is a continuation-in-part of application Ser. No. 429,196 filed Dec. 28, 1973, now abandoned.

BACKGROUND OF THE INVENTION

1. Field of the Invention

This invention relates to the hydrogenation of mixed nitroaromatic compounds.

2. Description of the Prior Art

Phenylene diamines, toluidines, naphthylamines and other aromatic amino compounds are customarily produced by catalytic reduction of the corresponding nitro compounds, employing a variety of catalysts and conditions, including temperature and pressure. In general, a single nitro compound can be reduced to the desired amino compound in a batch or a continuous process. When it is desired to reduce a mixture of nitro compounds, for example, an isomeric mixture or a mixture containing mono and dinitro compounds, the mixture can be hydrogenated before any separation of components is effected.

Among the problems associated with the preparation of aromatic amines from aromatic nitro compounds, particularly in commercial quantities, is the differing reactivities of various nitro compounds under the reduction conditions employed. This problem is more acute in catalytic hydrogenation processes than when a reducing agent such as sodium sulfhydrate or sodium hydrosulfite is employed. The activity of the catalyst is very important and it is difficult to find a single catalyst which can be used efficiently to reduce a wide variety of aromatic nitro compounds. Ring hydrogenation and partial reduction of the nitro group may be achieved with catalysts which are either too active or too inactive. Frequently, undesired by-products are produced, for example, high boiling materials or tars which may be almost unidentifiable.

U.S. Pat. No. 3,213,141 discloses a process for hydrogenating an aromatic dinitro compound or a mixture of isomeric aromatic dinitro compounds, in the presence of a nickel or platinum catalyst, wherein said process liquid dinitro compound is introduced into a reaction vessel containing a mixture of water and the corresponding aromatic diamino compound at such a rate that the nitro compound dissolves in the mixture, and a liquid stream is removed from the reaction vessel at such a rate that it is substantially free of unhydrogenated dinitro compound.

OBJECTS AND SUMMARY OF THE INVENTION

It is an object of this invention to provide a process for the hydrogenation of mixed aromatic nitrobodies. Another object is to provide such a process which can be operated either continuously or batchwise. A further object is to provide such a process wherein is produced at least one aromatic monoamine and at least one aromatic diamine. A still further object is to provide such a process for preparing aromatic diamines at higher reaction rates, with less by-product tars and at higher yields than can be achieved with similar prior art hydrogenation processes. Another object is to provide such a process which is operable with either homogeneous or heterogeneous reaction mixtures.

The above objects are achieved by means of the invention which, in summary, comprises reacting hydrogen and a homogeneous or heterogeneous liquid mixture of at least 25 weight % of an aromatic dinitro compound and/or at least 25 weight % of an aromatic mononitromonoamino compound and at least 25 weight % of an aromatic mononitronon-amino compound, with vigorous mixing, in the presence of 0.05–1.0 weight % of an hydrogenation catalyst derived from a metal of Group VIII of the Periodic Chart of the Elements, at a temperature of 75°–225° C. and a pressure of 50–800 p.s.i.g.

Preferred embodiments of the invention include those wherein the catalyst is a supported catalyst; wherein the catalyst support has a surface area of 20–1,000 square meters per gram; wherein the catalyst support is carbon; wherein the catalyst is platinum on carbon or palladium on carbon; wherein the catalyst is platinum on carbon or palladium on carbon and contains 0.01–10.0 weight % of iron, nickel or chromium; wherein one of said aromatic nitro compounds is a nitrotoluene; and wherein one nitro compound is a nitrotoluene and at least one other nitro compound is o- or p-nitroaniline or a dinitrobenzene.

BRIEF DESCRIPTION OF THE DRAWING

The FIGURE is a schematic representation of an apparatus which is suitable for carrying out one embodiment of this invention, namely, a continuously operated process.

DETAILED DESCRIPTION OF THE INVENTION

The invention is applicable to both batch and continuous processes and to both homogeneous and heterogeneous liquid nitrobody mixtures. Among the more common aromatic amino compounds useful in the chemical industry are aniline; o-, m-, and p-toluidine; o-, m-, and p-phenylenediamine; α-naphthylamine; the isomeric chloroanilines; the isomeric dichloroanilines; o-, m-, and p-anisidine; the isomeric chlorotoluidines; the isomeric aminobenzoic acids and the N-alkyl-p-phenylenediamines. The process of this invention is amenable to the preparation of such amines. It must be recognized that the process of this invention always gives at least one monoamine and at least one diamine, both of which must be commercially desirable if the process is to be economically and commercially useful. It has been discovered that the hydrogenation of a mixture of at least two nitro compounds as defined above in the Summary gives a better yield of at least one of the amino products than can be achieved when such amine is produced by the hydrogenation of the corresponding nitro compound alone. More specifically, although the catalytic hydrogenation of mononitro-non-amino aromatic compounds can be carried out under prior art conditions at high reaction rates, at high yields and with low by-product tar formation, such frequently is not the case in the catalytic hydrogenation of an aromatic dinitro or an aromatic mononitromonoamino compound. The present invention, therefore, resides in the discovery that dinitro or mononitromonoamino compounds, or both, can be catalytically hydrogenated at high reaction rates, at high yields and with low by-product tar formation when the dinitro and/or the mononitromonoamino aromatic compound is hydrogenated in the presence of a mononitro-nonamino aromatic compound. In order to achieve the benefit of this invention each nitro compound being hydrogenated must constitute at least 25 weight % of the mixture of nitro compounds being hydrogenated. In general, prior art catalysts and hydrogenation conditions are employed.

Nitrobody mixtures which can be advantageously employed in the process of the invention include, for example, o-nitrotoluene and o-nitroaniline, o-nitrotoluene and p-nitroaniline, o-nitroaniline and α-nitronaphthalene, nitrobenzene and o-nitroaniline and nitrobenzene and p-nitroaniline. A broader list of aromatic nitro compounds which can be coreduced as taught herein includes those which are listed in the following table.

|  | m.p. (°C.) |
|---|---|
| o-nitrotoluene | −10.6 (α) |
| o-nitrotoluene | −4.1 (β) |
| nitrobenzene | 5.7 |
| o-nitroanisole | 9.4 |
| m-nitrotoluene | 15.5–16 |
| m-chloronitrobenzene | 23.7 |
| o-chloronitrobenzene | 32.5 |
| N-methyl-o-nitroaniline | 34 |
| m-nitroanisole | 38 |
| p-nitrotoluene | 51.9 |
| p-nitroanisole | 54 |
| α-nitronaphthalene | 59–60 |
| N-methyl-m-nitroaniline | 67–68 |
| o-nitroaniline | 71.5 |
| β-nitronaphthalene | 79 |
| p-chloronitrobenzene | 83–84 |
| m-dinitrobenzene | 89.8 |
| m-nitroaniline | 114 |
| o-dinitrobenzene | 117–118 |
| p-nitroaniline | 148 |
| N-methyl-p-nitroaniline | 151–152 |
| p-dinitrobenzene | 173–174 |

In carrying out the process of the invention, the nitrobody mixture can be slurried in water or weak aqueous alkali in the presence of a finely divided hydrogenation catalyst. Vigorous mixing must be used to ensure adequate mass and heat transfer. Hydrogen pressure usually is in the range 50–800 p.s.i.g. (pounds per square inch gauge); however, 200–500 p.s.i.g. is preferred. Temperature usually is in the range 75°–225° C.; preferred is 100°–200° C.

The process is not limited to the use of a particular catalyst, conventionally prepared nitrobody hydrogenation catalysts which are known in the art being operable. For example, a catalyst derived from a metal of Group VIII of the Periodic Chart of the Elements is useful. Exemplary thereof, nickel, cobalt, rhodium, platinum and palladium catalysts which have been prepared by known techniques are operable. The catalyst can be introduced in the form of its oxide, hydroxide, carbonate, formate or free metal. It can be prereduced or merely subjected to the hydrogenation process conditions, which will reduce it in situ. Other metals can be used as additives, including iron, nickel and chromium. Support materials, which afford a large surface area on which the active metal is deposited, also can be used. Carbon is a frequently used support material and can be used in most commercially available forms, such as "Darco" and "Nuchar." A preferred catalyst is a 5% palladium on carbon catalyst since it is useful in many aromatic nitrobody reductions.

In general, the selection of a catalyst can be correlated by one skilled in the art of catalysis to the nitrobodies being hydrogenated. Supported catalysts are especially useful herein, particularly supported palladium and platinum catalysts, and especially such catalysts wherein carbon is the support. Still further, such precious metal catalysts which contain small amounts of iron, nickel or chromium oxides or hydroxides are preferred. In connection with the above, the concentration of catalyst on the support should be 0.1–10 weight % of the support weight. Similarly, the amount of iron, nickel or chromium present should be 0.1–10 weight % of the support weight. The preferred catalyst contains about 4 weight % of platinum and about 8 weight % of iron or finely divided carbon and is prepared as described in one of the examples. As indicated, the preferred support is carbon which may range from submicron to about 40 microns in particle size. A particle size of less than 10 microns is preferred. The carbon usually has a surface area of about 20–1,000 square meters per gram.

Following is a description of a typical supported catalyst preparation and its use in the hydrogenation process of this invention. The support, which can be any inert high surface material, is suspended in water and a solution of alkali metal carbonate or bicarbonate is added. A solution of the catalyst metal as a salt or acid is added and the mixture is heated to about 95° C. until all of the catalyst metal has precipitated. The reaction mixture can be reduced at this stage with a conventional reducing agent, such as formaldehyde, hydrogen or hydrazine, but this is not essential since reduction can be effected at point of use. The catalyst is isolated in the form of an aqueous paste and can be used in this form or it can be dried.

The catalyst is used at about 0.05–1.0% by weight of the hydrogenation reaction mixture, preferably about 0.5%. The hydrogenation is carried out at about 75°–225° C. and 50–800 p.s.i.g., preferably 100°–200° C. and 200–500 p.s.i.g. It is to be understood that a different catalyst can be employed for each specific nitrobody mixture hydrogenated and the temperature and pressure can be varied as may be appropriate for the compounds being hydrogenated.

In carrying out the process of this invention batchwise wherein, for example, nitrobody mixture is slurried in water or weak aqueous alkali in the presence of a finely divided hydrogenation catalyst, hydrogen is supplied to the reaction mixture until no more is taken up. The non-aqueous layer containing the amine products can sometimes be separated by gravity from the aqueous layer and it is filtered to remove traces of catalyst. More often, particularly when the product includes a large proportion of diamine, the mass is homogeneous. In these cases, after filtration to remove the catalyst, the charge can be fractionally distilled, first to remove the water and then to separate the desired amine products from any high boiling materials, for example, tars. The percentage of tars can be determined with reasonable accuracy by subjecting a weighed sample to sublimation at about 150° C. under a reduced pressure of about 1 mm. of Hg. The tars do not sublime and are weighed as residue when the weight becomes constant.

Preferably, the hydrogenations are performed in a weakly ammoniacal environment which further represses tar formation. In place of ammonia can be employed a cycloaliphatic amine, such as morpholine or piperazine.

Vigorous mixing of reactants (including the catalyst) is essential; in a stirred reactor, for example, a power input of 10–60 horsepower per 1,000 gallons of reaction medium is necessary; preferably, in such a reactor, it is 15-40 horsepower per 1,000 gallons of reaction medium.

Batch reactions are used where requirements are insufficient to justify the installation of equipment for continuous processes.

Following is a description of one embodiment of a continuously operated process of this invention, in terms of the production of o-toluidine (from o-nitrotoluene) and an aromatic diamine. A stream of the requisite admixed nitro compounds is passed into a hydrogenation reactor while simultaneously adding hydrogen gas under pressure. Sufficient hydrogenation catalyst is added to catalyst the reaction. Catalyst is added thereafter in sufficient quantities to replace the small amounts lost in the product stream. The bulk of the catalyst either is retained in the hydrogenation zone, for example, by inner filtration wherein liquid product is passed through a filter and the catalyst particles are rejected, or it is recycled, for example, by exterior filtration whereby the product is circulated through an exterior filter or thickener and substantially all of the catalyst is returned to the reactor with the circulating liquid while a relatively small amount of almost clear liquid is removed from the system as product. Under steady state or equilibrium conditions the reactor thus contains only a small amount (no more than 0.5 weight %) of unreduced nitro compounds and a very high amount (at least 99 weight %, for example, 99.9%) of amino compound reduction products. The configuration of the reactor is not critical and conventional reactors can be employed, it being only necessary that the reactants be well mixed and that sufficient hydrogen be fed to accomplish the desired nitro group reduction.

In the schematic drawing shown in the figure hold tank 1 contains already hydrogenated product to be used in starting up the reactor. Feed tank 2 contains the nitrobody feed which is either o-nitrotoluene or a homogeneous liquid mixture of o-nitrotoluene and at least one other aromatic nitro compound. Pump 3 is used to introduce nitrobody feed, under pressure, to the reaction vessel 4 which is a vessel having means for providing intimate contact between liquid, hydrogen gas and solid catalyst. Gas from gas-liquid separator 5 either can be vented through line 13 or recompressed for recycle to the reaction vessel 4 via compressor 6. The liquid from separator 5 is led to thickener 7 from which clear product amine is removed to product hold tank 11. The other output of the thickener, a recycle stream containing catalyst, is returned to reaction vessel 4 via liquid recycle pump 10 and heat exchanger 8 which removes heat of reaction so as to maintain the desired reaction temperature. Fresh hydrogen is introduced to the system either at the intake side of compressor 6 via line 12 or via lines 12 and 14, bypassing the compressor 6. An aqueous slurry of catalyst, pressurized with nitrogen from line 15, is introduced from vessel 9 through line 16.

In the following examples all parts and percentages are by weight unless otherwise noted; parts are in grams.

EXAMPLE 1

(a) To a high pressure autoclave fitted with an efficient stirrer were charged 35 parts of o-nitroaniline, 34 parts of o-nitrotoluene, 400 parts of water and 0.15 part of a 50% catalyst/50% water paste. The catalyst was 5% palladium on carbon (containing no platinum or other metal except the palladium). The charge was heated at 120°-121° C. while hydrogen was applied at 500 p.s.i. After 10.5 minutes of hydrogenation, hydrogen was no longer absorbed and the pressure was held at 500 p.s.i. After 2 hours more at 120° C. the charge was cooled and removed from the autoclave. The desired o-phenylenediamine and o-toluidine were recovered by distillation. Only 1.4% tar was produced in the reaction.

(b) In order to show the effect of tar on the reaction rate of a catalytic hydrogenation employing only the mononitromonoamino compound (o-nitroaniline) of part (a), a series of experiments was carried out employing the catalyst and hydrogenation conditions set forth in part (a). Three types (purities) of o-nitroaniline were used, namely, one which was known to resist hydrogenation, one which was known to hydrogenate readily and one which had been distilled (to remove any tar therefrom) and which was known to hydrogenate even more readily than the aforesaid second type of o-nitroaniline. In carrying out the experiments, 69 grams of o-nitroaniline were mixed with 350 grams of water, 50 ml. of 29 weight % aqueous ammonium hydroxide and 0.15 gram of catalyst in a 1 liter, stainless steel agitated autoclave. The hydrogenation was carried out at about 120° C. and a nominal hydrogen pressure of 500 p.s.i.g. Each time the pressure dropped to about 400 p.s.i.g. additional hydrogen was added to raise the pressure to 500 p.s.i.g.

The first sample of o-nitroaniline required in excess of 90 minutes for hydrogenation. When this sample of o-nitroaniline was purified (sublimed at 65°-75° C. and 0.1 mm. of mercury; 1% tar residue), the use thereof in the aforesaid hydrogenation procedure provided hydrogenation in 17 minutes. The second sample of o-nitroaniline was hydrogenated in 22 minutes. The third sample of o-nitroaniline, that is, the distilled sample, was hydrogenated in 13 minutes. When the 1% residual tar from the sublimed first sample of o-nitroaniline was added to the distilled sample, the crude o-nitroaniline thus produced required 90 minutes for hydrogenation. Since tar formation is known to be common in the production of aromatic diamines, as opposed to the production of aromatic monoamines, it has been concluded that the improved reaction rates which are achieved in the production of aromatic diamines by the process of this invention are directly related to the fact that the improved process of this invention provides for the production of aromatic diamines with less by-product tar formation.

EXAMPLE 2

A high pressure autoclave fitted with an efficient stirrer was charged with 35 parts (grams) of p-nitroaniline, 34 parts (grams) of o-nitrotoluene, 400 parts of water and 0.15 part of the same palladium catalyst paste described in Example 1. The charge was heated at 120°-121° C. while hydrogen was added at 500 p.s.i. After 7.5 minutes of hydrogenation, hydrogen was no longer absorbed and the pressure was held at about 500 p.s.i. The charge was cooled and removed from the autoclave. The desired p-phenylenediamine and o-toluidine were recovered by distillation. Only 2.1% tar (0.57 gram) was produced in the reaction, based on the diamine product (since the o-nitrotoluene produces little or no tar during hydrogenation). The yield of the combined amines was 95.8%.

When 67 grams of p-nitroaniline were hydrogenated with the same catalyst in the same manner (without the o-nitrotoluene), the tar content was 7.3% (3.94 grams); the yield was 85.4%.

EXAMPLE 3

(a) Preparation of Hydrogenation Catalyst

In a suitable vessel were mixed at 25° C. 1,000 ml. of deionized water, 76.8 grams of sodium chloride and 64.0 grams of commercially available "Nuchar" WAN-FF activated carbon. To the stirred mixture at 30° C. were added 256 ml. of a 0.02 gram/ml. solution of $FeCl_3.6H_2O$, then gradually over about 0.75 hour 512 ml. of a 0.06 gram/ml solution of $NaHCO_3$. The resulting yellow slurry was heated to the boiling point and refluxed for 1 hour. Next, while maintaining reflux, were added 256 ml. of a 0.03 gram/ml. solution of $Na_2CO_3$ over a 15 minute period and then 128 ml. of a 0.02 gram/ml. solution of $H_2PtCl_6$ over about 1 hour. The charge was held at reflux temperature for an additional 1 hour. After cooling to about 30° C. the solid catalyst was separated by filtration and washed with water. The water wet catalyst cake was dried on a suction filter but was not further dried.

(b) Continuous Hydrogenation

Continuous hydrogenation of two representative nitrobody mixtures is described in this example.

The reactor was a 49.25 inch×2 inch tube of schedule 40 pipe made of type 316 stainless steel and flanged on both ends for ease of installation into or removal from the system. Inside the reactor were installed nine 1.9375 inch diameter by 0.25 inch thick "Teflon" polytetrafluoroethylene trays spaced 6 inches apart. The trays were held in place by three 0.25 inch diameter threaded stainless steel rods with stainless steel nuts screwed up to both sides of each tray. The volume of the reactor was 0.718 gallon. The reactor was charged essentially liquid-full with o-toluidine from a previous run and with sufficient catalyst (from Part a) to give a concentration of 0.5% of dry catalyst, based on the o-toluidine. The recycle loop was started and hydrogen was introduced. At the same time a liquid mixture containing 25% p-nitroaniline and 75% o-nitrotoluene was fed to the reactor. The reaction temperature was maintained at about 120° C. and the hydrogen pressure, at 200 lbs./sq. in. gauge. The rate of output was about 5 lbs. per hour per gallon of reactor volume. Additional catalyst was added as required to maintain the desired concentration in the reactor. The product contained 78.9% o-toluidine, 20.8% p-phenylenediamine, 0.15% tar and less than 0.1% unreduced nitrobody.

The next feed contained 25% o-nitroaniline and 75% o-nitrotoluene. In this part of the run the temperature was maintained at about 150° C. and the pressure, at 200 lbs./sq. in. gauge. The rate of output again was about 5 lbs. per hour per gallon of reactor volume. The product contained about 8% tar. The product stream, on a water-free weight basis, contained about 99.9% of the desired amines, the o-toluidine content being about 74% and the o-phenylenediamine content being about 24%.

The pure amines can be separated from the aforesaid mixtures of amines by fractional distillation under reduced pressure using a packed column. In this way o-toluidine and p-phenylenediamine were separated. The identification of the amines in the second part of this example was made by vapor phase chromatography.

EXAMPLE 4

(a) Preparation of Hydrogenation Catalyst

To a stirred slurry of 30 parts of an acetylene black carbon in 500 parts of water were added 7.5 parts of an $H_2PtCl_6$ solution (prepared by dissolving 26.52 parts of $H_2PtCl_6.6H_2O$ in 500 parts of water). There were then added 67.5 parts of an $PdCl_2$ solution (prepared by dissolving 16.66 parts of $PdCl_2$ and 20 parts of 12 N HCl in 480 parts of water). Finally, there were added 75 parts of an $FeCl_3$ solution (prepared by dissolving 24.5 parts of $FeCl_3.6H_2O$ in 250 parts of water). The temperature was adjusted to about 30° C. and 300 parts of a 6% $NaHCO_3$ solution were added gradually over 30 minutes. The mixture was then heated gradually to 90° C. over a 1 hour period; it was then maintained at this temperature for 1 hour. The mixture was filtered and the wet cake recovered contained 75% water. The wet cake was used directly in part (b) of this example, that is, the active hydrogenation catalyst was prepared in situ in the hydrogenation reactor.

(b) Batchwise Hydrogenation

Into a 300 ml. stainless steel autoclave were charged 38.5 grams of crude nitrated benzene containing 28.9 grams (0.235 mole) of mononitrobenzene and 9.6 grams (0.057 mole) of dinitrobenzene (88% meta, 10% ortho and 2% para), 48.0 grams of water, 19.7 grams of aniline and 0.11 gram of the wet cake from part (a). The in situ-prepared catalyst employed in this example thus contained 0.5% platinum, 4.5% palladium and 5% iron. The autoclave was closed and agitation was commenced (stirring at 1,200 r.p.m.). Hydrogen was applied to achieve 300 p.s.i.g.; hydrogen pressure was maintained at 300 p.s.i.g. for the entire experiment which required 25 minutes for completion. The temperature was raised gradually from 110° C. at the beginning of hydrogenation to 198° C. after 25 minutes. After 18 minutes hydrogen pressure remained constant. After completion of hydrogenation the reaction mixture was cooled to 25°-30° C. and filtered. The filtrate was distilled to remove the water. Any aniline removed during distillation was returned to the distillation residue. The distillation residue contained 47 grams of product which by analysis was shown to contain 86.8% aniline and 13.2% phenylenediamine (89% meta, 10% ortho and 1% para). The product contained no more than a trace of tar and unreduced nitro compounds. The yield was greater than 99%. A comparison of this example may be made with Example 5(b) to show the results when only the dinitrobenzene is hydrogenated.

EXAMPLE 5

(a) Preparation of Catalyst

To a stirred slurry of Shawinigan Black carbon (222 g) and 3,670 ml of water were added 55.5 ml of $H_2PtCl_6$ solution (prepared by dissolving 26.52 g of $H_2PtCl_6.6H_2O$ in 500 ml of water), 500 ml of $PdCl_2$ solution (prepared by dissolving 33.32 g of $PdCl_2$ and 20 ml of 12 N HCl in 960 ml of water) and 555 ml of $FeCl_3$ solution (prepared by dissolving 98.0 g of $FeCl_3.6H_2O$ in 1,000 ml of water). To the above mixture 2,200 ml of 6% aqueous $NaHCO_3$ solution were added over a 45 minute period. The mixture was heated to 90° C. and held at this temperature for 1 hour. To the mixture at 90° C. were added 90 ml of 37% aqueous formaldehyde solution over a period of about 30 minutes. After the completion of addition of the formaldehyde solution the mixture was kept at 90° for 1 hour. The mixture was allowed to cool to 60° C. and then filtered. The precipitate thus prepared was dried, providing a catalyst containing 0.5 weight % Pt, 4.5 weight % Pd and 5 weight % Fe on the carbon support.

(b) A high pressure autoclave fitted with an efficient stirrer was charged with 84 g (0.5 mole) of dinitrobenzene which consisted of 85% meta, 12% ortho, and 3% para isomers, 450 ml of water and 0.25 g of the catalyst of Part (a). The charge was heated to 100° C. while hydrogen was added at 400–500 psi. After 42 minutes hydrogen absorption ceased. The yield of the product was 93.6%. The tar weight was 1.73 g, corresponding to 3.2% tar, based on the diamine product.

(c) A high pressure autoclave equipped with an efficient stirrer was charged with 84 g (0.5 mole) of dinitrobenzene which consisted of 85% meta, 12% ortho, and 3% para isomers, 69 g (0.5 mole) of o-nitrotoluene, 350 g of water and 0.2 g of the catalyst of Part (a). Hydrogenation was carried out at 100° C. and 400–500 psi hydrogen pressure. After 40.5 minutes absorption of hydrogen ceased. The yield of the combined amines was 96.0%. Tar weight was 1.08 g, corresponding to 2.0% tar, based on the diamine product (since the mononitro compound produces little or no tar during hydrogenation).

A comparison of Parts (b) and (c) shows that when equal weights of dinitrobenzene (84 g) are hydrogenated, the invention process provides a 37.5% reduction in tar (expected). It is also to be noted from the comparison that with the present invention process the reduction time to essentially the same conversion is about the same, even though the amount of nitro groups to be reduced was increased 50%, that is, 1 mole of $NO_2$ groups in (b) vs 1.5 moles of $NO_2$ groups in (c).

EXAMPLE 6

(a) A high pressure autoclave equipped with an efficient stirrer was charged with 69 g (0.5 mole) of o-nitroaniline, 400 ml of water and 0.15 g of the catalyst described in Example 1. Hydrogenation was carried out at 120° C. at a hydrogen pressure of 400–500 psi. Hydrogenation ceased after 39 minutes. The yeilds of the diamine was 92.8%. Tar weight was 1.94 g, corresponding to 3.6% tar, based on the diamine product.

(b) A high pressure autoclave equipped with an efficient stirrer was charged with 35 g (0.254 mole) of o-nitroaniline, 34 g (0.248 mole) of o-nitrotoluene, 400 ml of water and 0.3 g of the catalyst described in Example 3 (a). Hydrogenation was carried out at 140° C. at a hydrogen pressure of 400–500 psi. Hydrogenation ceased after 41 minutes. The yield of the combined amines was 98.6%. Tar weight was 0.2%, corresponding to 0.7% tar, based on the diamine produced (since the o-nitrotoluene produces little or no tar during hydrogenation), A comparison of Parts (a) and (b) again brings out the advantageous nature of the present invention. In these examples the total amounts of nitro groups being reduced are the same (0.5 mole of $NO_2$ groups in each). Based on (a) it would be reasonably expected that (b) would give about 0.97 g of tar. However, the amount of tar was only 0.2 g, corresponding to a reduction in tar formation of about 79%.

EXAMPLE 7

(a) A high pressure autoclave equipped with an efficient stirrer was charged with 68 g (0.493 mole) of p-nitroaniline, 350 ml of water, 50 ml of aqueous ammonium hydroxide and 0.15 g of the catalyst described in Example 1. Hydrogenation was carried out at 120° C. at a hydrogen pressure of 400–500 psi. Hydrogenation ceased after 35 minutes. The yield of the diamine was 82.0%. Tar weight was 4.86 g, corresponding to 9.0% tar, based on the diamine product.

(b) A high pressure autoclave equipped with an efficient stirrer was charged with 35 g (0.254 mole) of p-nitroaniline, 31 g (0.252 mole) of nitrobenzene, 400 ml of water and 0.3 g of the catalyst described in Example 3 (a). Hydrogenation was carried out at 120° C. at a hydrogen pressure of 400–500 psi. Time of hydrogenation was 27.5 minutes. The yield of the combined amines was 94.8%. Tar weight was 0.7 g, corresponding to 2.6% tar, based on the diamine product (since the nitrobenzene produces little or no tar during hydrogenation).

A comparison of Parts (a) and (b) again demonstrates the unexpected advantage of the present invention process. In this comparison the same amounts of nitro groups (0.5 mole) were hydrogenated. It would be expected, based on (a), that in (b) 2.43 g of tar would be produced since the amount of p-nitroaniline in (b) is about one half of that in (a). However, only 0.7 g of tar was produced, corresponding to about a 72% reduction over the expected amount.

I claim:

1. Process for catalytically hydrogenating a mixture of aromatic compounds consisting of at least one mononitro-non-amino compound and at least one compound selected from dinitro and mononitromonoamino compounds in a reaction vessel to produce a mixture of separable corresponding aromatic amino compounds consisting of at least one monoamino compound and at least one diamino compound, which process comprises reacting hydrogen and a homogeneous or heterogeneous liquid mixture of at least 25 weight % of an aromatic mononitro-non-amino compound and at least 25 weight % of at least one compound selected from aromatic dinitro compounds and aromatic mononitromonoamino compounds, with vigorous mixing, in the presence of 0.05–1.0 weight % of a hydrogenation catalyst derived from a metal of Group VIII of the Periodic Chart of the Elements, at a temperature of 75°–225° C. and a pressure of 50–800 p.s.i.g.

2. Process of claim 1 which is carried out batchwise.

3. Process of claim 1 which is carried out continuously.

4. Process of claim 1 wherein the catalyst is a supported catalyst.

5. Process of claim 4 wherein the supported catalyst is platinum on carbon or palladium on carbon.

6. Process of claim 5 wherein the platinum or palladium comprises 0.1–10 weight % of the support weight.

7. Process of claim 6 wherein the catalyst contains 0.1–10 weight %, based on the support weight, of iron, nickel or chromium.

8. Process of claim 4 wherein the support is carbon.

9. Process of claim 8 wherein the carbon has a surface area of 20–1,000 square meters per gram.

10. Process of claim 1 wherein one of the nitro compounds is a nitrotoluene.

11. Process of claim 10 wherein one of the nitro compounds is o- or p-nitroaniline.

12. Process of claim 10 wherein one of the nitro compounds is a dinitrobenzene.

13. Process of claim 1 which is carried out in the presence of ammonia.

14. Process of claim 1 which is carried out at 100°–200° C. and 200–500 p.s.i.g.

* * * * *